(12) United States Patent
Neipp et al.

(10) Patent No.: US 9,187,461 B2
(45) Date of Patent: Nov. 17, 2015

(54) CATHEPSIN C INHIBITORS

(71) Applicant: GlaxoSmithKline Intellectual Property Development Limited, Brentford, Middlesex (GB)

(72) Inventors: Christopher E. Neipp, King of Prussia, PA (US); Michael R. Palovich, King of Prussia, PA (US)

(73) Assignee: GlaxoSmithKline Intellectual Property Development Limited, Brentford, Middlesex (GB)

( * ) Notice: Subject to any disclaimer, the term of this patent is extended or adjusted under 35 U.S.C. 154(b) by 0 days.

(21) Appl. No.: 14/464,734

(22) Filed: Aug. 21, 2014

(65) Prior Publication Data

US 2014/0364476 A1 Dec. 11, 2014

Related U.S. Application Data

(63) Continuation of application No. 13/984,061, filed as application No. PCT/US2012/024428 on Feb. 9, 2012, now Pat. No. 8,841,463.

(60) Provisional application No. 61/441,840, filed on Feb. 11, 2011.

(51) Int. Cl.
| | | |
|---|---|---|
| *C07D 209/04* | (2006.01) | |
| *A61K 31/35* | (2006.01) | |
| *C07D 405/12* | (2006.01) | |
| *C07D 309/08* | (2006.01) | |
| *C07D 309/14* | (2006.01) | |

(52) U.S. Cl.
CPC .............. *C07D 405/12* (2013.01); *A61K 31/35* (2013.01); *C07D 309/08* (2013.01); *C07D 309/14* (2013.01)

(58) Field of Classification Search
USPC ........................................................ 548/465
See application file for complete search history.

(56) References Cited

U.S. PATENT DOCUMENTS

| | | |
|---|---|---|
| 5,212,158 A | 5/1993 | Fiez Vandai |
| 6,362,166 B1 | 3/2002 | Webber et al. |
| 2002/0107266 A1 | 8/2002 | Lim-Wilby et al. |
| 2010/0249128 A1 | 9/2010 | Botrous et al. |
| 2010/0286118 A1 | 11/2010 | Ford et al. |
| 2012/0142668 A1 | 6/2012 | Anderson et al. |

FOREIGN PATENT DOCUMENTS

| | | |
|---|---|---|
| WO | WO 97/40842 A1 | 11/1997 |
| WO | WO 2012/119941 A1 | 9/2012 |

OTHER PUBLICATIONS

Dragovich, et al. J. Med. Chem. 1998, 41, 2806-2818.
Kam, et al. Archives of Biochemistry and Biophysics 2004, 427, 123-134.
Liu, et al. J. Med. Chem. 1992, 35, 1067-1075.
Winssinger, et al. Angew. Chem. Int. Ed. 2001, 40, 3152-3155.
Guay, et al. Current Topics in Medicinal Chemistry, 10: 708-716 (2010).
Yadav, et al. Journal of Enzyme Inhibition & Medicinal Chemistry, 23(2): 190-197 (2008).

*Primary Examiner* — Nyeemah A Grazier
(74) *Attorney, Agent, or Firm* — Duke M. Fitch; John Lemanowicz; William R. Majarian (57) ABSTRACT

Disclosed are 4-amino-2-butenamides of Formula (I) having pharmacological activity, pharmaceutical compositions containing them, and methods for the treatment of diseases mediated by the cathepsin C enzyme such as chronic obstructive pulmonary disease.

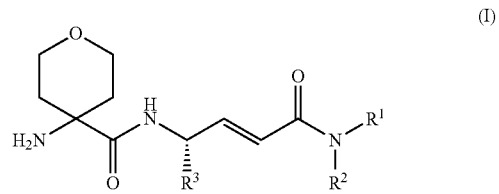

(I)

6 Claims, 3 Drawing Sheets

CATHEPSIN C INHIBITORS

FIELD OF THE INVENTION

The present invention relates to certain 4-amino-2-butenamides that are cathepsin C inhibitors, pharmaceutical compositions containing these compounds, and their use in the treatment of diseases mediated by the cathepsin C enzyme such as chronic obstructive pulmonary disease.

BACKGROUND OF THE INVENTION

Cathepsins are a family of enzymes included in the papain superfamily of cysteine proteases. Cathepsins B, C, F, H, K, L, S, V, and X have been described in the scientific literature. Cathepsin C is also known in the literature as Dipeptidyl Peptidase I or "DPPI."

A number of recently published studies have begun to describe the role cathepsin C plays in certain inflammatory processes. See e.g. Adkison et al., The Journal of Clinical Investigation 109:363-371 (2002); Tran et al., Archives of Biochemistry and Biophysics 403:160-170 (2002); Thiele et al., The Journal of Immunology 158: 5200-5210 (1997); Bidere et al., The Journal of Biological Chemistry 277: 32339-32347 (2002); Mabee et al., The Journal of Immunology 160: 5880-5885; McGuire et al., The Journal of Biological Chemistry, 268: 2458-2467; and Paris et al., FEBS Letters 369: 326-330 (1995). From these studies, it appears that cathepsin C is co-expressed in granules with certain serine proteases and functions to process the pro-forms of these proteases to active forms, which are then released from the granules of inflammatory cells recruited to sites of inflammation. Once activated, these proteases have a number of functions including degradation of various extracellular matrix components, which together can propagate tissue damage and chronic inflammation.

For example, Chronic Obstructive Pulmonary Disease ("COPD") is a chronic inflammatory disease where cathepsin C appears to play a role. Chronic bronchitis and emphysema usually occur together in COPD patients. Chronic bronchitis is generally characterized by a chronic productive cough, whereas emphysema is generally characterized by permanent enlargement of the airspaces distal to the terminal bronchioles and airway wall destruction.

Cigarette smoking is a significant risk factor for developing COPD. Exposure to cigarette smoke and other noxious particles and gases may result in chronic inflammation of the lung. In response to such exposure, inflammatory cells such as CD8+ T cells, macrophages, and neutrophils are recruited to the area. These recruited inflammatory cells release proteases, which are believed to play a major role in the disease etiology by a number of mechanisms. Proteases believed to be involved in this process include the serine proteases neutrophil elastase ("NE"), cathepsin G, and proteinase 3, all released from neutrophils; granzymes A and B, released from cytotoxic T cells or natural killer cells; and chymases, released from mast cells. Cathepsin C appears to be involved in activating all of these enzymes. Additionally, cathepsin C knockout mice are resistant to lung airspace enlargement and inflammatory cell infiltration in both cigarette smoke and ozone exposure models of COPD. See Guay et al., *Current Topics in Medicinal Chemistry*, 2010, 10, 708-716; See also Podolin et al. (2008), Inflammation Research, 57(Suppl 2) S104.

Rheumatoid arthritis ("RA") is another chronic inflammatory disease where cathepsin C may play a role. Neutrophils are recruited to the site of joint inflammation and release cathepsin G, NE, and proteinase 3, which are believed to be responsible in part for cartilage destruction associated with RA (Hu, Y. and Pham, C. T. (2005) Arthritis Rheum 52: 2553-2558).

Other conditions where cathepsin C may play a role include osteoarthritis, asthma, and Multiple Sclerosis. See e.g. Matsui, K.; Yuyama, N.; Akaiwa, M.; Yoshida, N. L.; Maeda, M.; Sugita, Y.; Izuhara, K., Identification of an alternative splicing variant of cathepsin C/dipeptidyl-peptidase I, Gene. 293(1-2):1-7, 2002 Jun. 26; Wolters, P. J.; Laig-Webster, M.; Caughey, G. H., Dipeptidyl peptidase I cleaves matrix-associated proteins and is expressed mainly by mast cells in normal dog airways, American Journal of Respiratory Cell & Molecular Biology. 22(2):183-90, 2000.

One approach to treating these conditions is to inhibit the activity of the serine proteases involved in the inflammatory process, especially NE activity. See e.g., Ohbayashi, "Neutrophil elastase inhibitors as treatment for COPD", Expert Opin. Investig. Drugs 11(7): 965-980 (2002); Shapiro, "Neutrophil Elastase: Path Clearer, Pathogen Killer, or Just Pathologic?", Am. J. Respir. Cell Mol. Biol. 26: 266-268 (2002). In light of the role cathepsin C plays in activating certain serine proteases, especially NE, it is desirable to prepare compounds that inhibit its activity, which thereby inhibit serine protease activity. Thus, there is a need to identify compounds that inhibit cathepsin C, which can be used in the treatment of a variety of conditions mediated by cathepsin C.

There are additional activities of cathepsin C that may also be related to disease etiology. Cathepsin C has been demonstrated to have a role in neutrophil migration in the development of aortic aneurysms by a mechanism which has not been clearly elucidated (Pagano, M. B. et al. (2007) PNAS 104: 2855-2860). Thus, disease processes that involve neutrophil migration, as well as proteolytic enzyme release can be modulated by cathepsin C inhibition. Also, cathepsin C is highly expressed in the lung epithelium where it may play a role in the processing of other enzymes not yet identified. Cathepsin C has also been reported to cleave kallikrein-4, which is believed to play a role in dental enamel maturation (Tye, C. E. et al. (2009) J. Dental Res. 88: 323-327). Finally, cathepsin C is itself released from cells and may play a direct role in the degradation of matrix proteins.

SUMMARY OF THE INVENTION

The present invention involves novel compounds according to Formula (I) or a pharmaceutically acceptable salt thereof:

wherein:

$R^1$ and $R^2$ are each independently selected from the group consisting of hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, $(C_3-C_8)$cycloalkyl$(C_1-C_6)$alkyl, $(C_5-C_8)$cycloalkenyl$(C_1-C_6)$alkyl, heterocycloalkyl$(C_1-C_6)$alkyl, aryl, heteroaryl, aryl$(C_1-C_6)$alkyl, and heteroaryl$(C_1-C_6)$alkyl;

wherein any $(C_1-C_8)$alkyl, $(C_2-C_8)$alkenyl, or $(C_2-C_8)$ alkynyl is optionally substituted one to three times, independently, by —$CF_3$, cyano, —$CO_2(C_1-C_4)$alkyl, —$CONH(C_1-C_4)$alkyl, —$CON(C_1-C_4)$alkyl$(C_1-C_4)$ alkyl, —$SO_2(C_1-C_4)$alkyl, —$SO_2NH(C_1-C_4)$alkyl, —$SO_2N(C_1-C_4)$alkyl$(C_1-C_4)$alkyl, amino, $(C_1-C_4)$ alkylamino, $((C_1-C_4)$alkyl$)((C_1-C_4)$alkyl$)$amino, hydroxyl, or $(C_1-C_4)$alkoxy;

and wherein any cycloalkyl, cycloalkenyl, bicycloalkyl, or heterocycloalkyl group is optionally substituted one to three times, independently, by $(C_1-C_4)$alkyl, $(C_1-C_4)$haloalkyl, cyano, —$CO_2(C_1-C_4)$alkyl, —$CONH(C_1-C_4)$ alkyl, —$CON(C_1-C_4)$alkyl$(C_1-C_4)$alkyl, —$SO_2(C_1-C_4)$ alkyl, —$SO_2NH(C_1-C_4)$alkyl, —$SO_2N(C_1-C_4)$alkyl $(C_1-C_4)$alkyl, amino, $(C_1-C_4)$alkylamino, $((C_1-C_4)$ alkyl$)((C_1-C_4)$alkyl$)$amino, hydroxyl, $(C_1-C_4)$alkoxy, aryl, or aryl$(C_1-C_4)$alkyl, wherein the aryl moiety of said aryl or aryl$(C_1-C_4)$alkyl is optionally substituted one to three times, independently, by halogen, —$CF_3$, $(C_1-C_4)$ alkyl, hydroxyl, or $(C_1-C_4)$alkoxy;

and wherein any aryl or heteroaryl group is optionally substituted one to three times, independently, by halogen, $(C_1-C_6)$alkyl, $(C_3-C_6)$cycloalkyl, $(C_5-C_6)$cycloalkenyl, $(C_1-C_6)$haloalkyl, cyano, —$CO_2(C_1-C_4)$alkyl, —$CONH(C_1-C_4)$alkyl, —$CON(C_1-C_4)$alkyl$(C_1-C_4)$ alkyl, —$SO_2(C_1-C_4)$alkyl, —$SO_2NH(C_1-C_4)$alkyl, —$SO_2N(C_1-C_4)$alkyl$(C_1-C_4)$alkyl, amino, $(C_1-C_4)$ alkylamino, $((C_1-C_4)$alkyl$)((C_1-C_4)$alkyl$)$amino, hydroxyl, $(C_1-C_4)$alkoxy, $(C_1-C_4)$alkylthio-, aryl, heteroaryl, aryl$(C_1-C_4)$alkyl, or heteroaryl$(C_1-C_4)$alkyl;
wherein any aryl or heteroaryl moiety of said aryl, heteroaryl, aryl$(C_1-C_4)$alkyl, or heteroaryl$(C_1-C_4)$alkyl is optionally substituted one to three times, independently, by halogen, —$CF_3$, $(C_1-C_4)$alkyl, hydroxyl, or $(C_1-C_4)$alkoxy;
and wherein any $(C_3-C_6)$cycloalkyl is optionally substituted one to three times, independently, by $(C_1-C_4)$ alkyl, aryl, or heteroaryl;
wherein said aryl or heteroaryl is optionally substituted one to three times, independently, by halogen, —$CF_3$, $(C_1-C_4)$alkyl, hydroxyl, or $(C_1-C_4)$alkoxy;

or $R^1$ and $R^2$ taken together with the nitrogen to which they are attached represent a 5- to 7-membered saturated or unsaturated ring optionally containing one other heteroatom which is oxygen, nitrogen, or sulfur, wherein said ring is optionally fused to a $(C_3-C_8)$cycloalkyl, heterocycloalkyl, aryl, or heteroaryl ring;

or $R^1$ and $R^2$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring; and $R^3$ is hydrogen, $(C_1-C_8)$alkyl, $(C_1-C_8)$haloalkyl, $(C_2-C_8)$ alkenyl, $(C_2-C_8)$alkynyl, $(C_3-C_6)$cycloalkyl, $(C_5-C_6)$cycloalkenyl, $(C_3-C_6)$cycloalkyl$(C_1-C_4)$alkyl, $(C_5-C_6)$cycloalkenyl$(C_1-C_4)$alkyl, or aryl$(C_1-C_4)$alkyl, wherein the aryl moiety of the aryl$(C_1-C_4)$alkyl is optionally substituted one to three times, independently, by halogen, $(C_1-C_4)$alkyl, or —$CF_3$.

The present invention is also directed to the use of a compound of Formula (I) or a pharmaceutically acceptable salt thereof in the prevention, management or treatment of a respiratory or inflammatory disease, such as chronic obstructive pulmonary disease or rhinitis.

In a further aspect, this invention relates to a pharmaceutically acceptable formulation comprising a compound of Formula (I) or a pharmaceutically acceptable salt thereof and a pharmaceutically acceptable excipient.

DETAILED DESCRIPTION OF THE INVENTION

Terms and Definitions

As used herein, the term "alkyl" refers to a straight- or branched-chain hydrocarbon radical having the specified number of carbon atoms. As used herein, the terms "$(C_1-C_4)$ alkyl" and "$(C_1-C_8)$alkyl" refer to an alkyl group having at least 1 and up to 4 or 8 carbon atoms respectively. Examples of such branched or straight-chained alkyl groups useful in the present invention include, but are not limited to, methyl, ethyl, n-propyl, isopropyl, n-butyl, isobutyl, s-butyl, t-butyl, n-pentyl, isopentyl, n-hexyl, n-heptyl, n-octyl, and branched analogs of the latter 3 normal alkanes.

When the term "alkyl" is used in combination with other substituent groups, such as "$(C_1-C_4)$haloalkyl" or "aryl$(C_1-C_4)$alkyl", the term "alkyl" is intended to encompass a divalent straight or branched-chain hydrocarbon radical, wherein the point of attachment is through the alkyl moiety. Examples of "$(C_1-C_4)$haloalkyl" groups useful in the present invention include, but are not limited to, —$CF_3$ (trifluoromethyl), —$CCl_3$ (trichloromethyl), 1,1-difluoroethyl, 2,2,2-trifluoroethyl, and hexafluoroisopropyl. Examples of "aryl$(C_1-C_4)$ alkyl" groups useful in the present invention include, but are not limited to, benzyl (phenylmethyl), 1-methylbenzyl (1-phenylethyl), 1,1-dimethylbenzyl (1-phenylisopropyl), and phenethyl (2-phenylethyl).

As used herein, the term "alkenyl" refers to straight or branched hydrocarbon chains containing the specified number of carbon atoms and at least 1 and up to 3 carbon-carbon double bonds. Examples include ethenyl and propenyl.

As used herein, the term "alkynyl" refers to straight or branched hydrocarbon chains containing the specified number of carbon atoms and at least 1 and up to 3 carbon-carbon triple bonds. Examples include ethynyl and propynyl.

As used herein, the term "cycloalkyl" refers to a non-aromatic, saturated, cyclic hydrocarbon ring containing the specified number of carbon atoms. The term "$(C_3-C_8)$cycloalkyl" refers to a non-aromatic cyclic hydrocarbon ring having from three to eight ring carbon atoms. Exemplary "$(C_3-C_8)$cycloalkyl" groups useful in the present invention include cyclopropyl, cyclobutyl, cyclopentyl, cyclohexyl, cycloheptyl, and cyclooctyl.

As used herein, the term "cycloalkenyl" refers to a non-aromatic, cyclic hydrocarbon ring containing the specified number of carbon atoms and at least one carbon-carbon double bond. The term "$(C_5-C_8)$cycloalkenyl" refers to a non-aromatic cyclic hydrocarbon ring having from five to eight ring carbon atoms. Exemplary "$(C_5-C_8)$cycloalkenyl"

groups useful in the present invention include cyclopentenyl, cyclohexenyl, cycloheptenyl, and cyclooctenyl.

As used herein, the term "bicycloalkyl" refers to a saturated, bridged, bicyclic hydrocarbon ring system containing the specified number of carbon atoms. The term "$(C_6-C_{10})$ bicycloalkyl" refers to a bicyclic hydrocarbon ring system having from six to ten carbon atoms. Exemplary "$(C_6-C_{10})$ bicycloalkyl" groups useful in the present invention include bicyclo[2.1.1]hexyl, bicyclo[2.1.1]heptyl, bicyclo[3.2.1]octyl, bicyclo[2.2.2]octyl, bicyclo[3.2.2]nonyl, bicyclo[3.3.1]nonyl, bicyclo[3.3.2]decyl, and bicyclo[4.3.1]decyl.

"Alkoxy" means an alkyl radical containing the specified number of carbon atoms attached through an oxygen linking atom. The term "$(C_1-C_4)$alkoxy" refers to a straight- or branched-chain hydrocarbon radical having at least 1 and up to 4 carbon atoms attached through an oxygen linking atom. Exemplary "$(C_1-C_4)$alkoxy" groups useful in the present invention include, but are not limited to, methoxy, ethoxy, n-propoxy, isopropoxy, n-butoxy, s-butoxy, and t-butoxy.

"Alkylthio-" means an alkyl radical containing the specified number of carbon atoms attached through a sulfur linking atom. The term "$(C_1-C_4)$alkylthio-" refers to a straight- or branched-chain hydrocarbon radical having at least 1 and up to 4 carbon atoms attached through a sulfur linking atom. Exemplary "$(C_1-C_4)$alkylthio-" groups useful in the present invention include, but are not limited to, methylthio-, ethylthio-, n-propylthio-, isopropylthio-, n-butylthio-, s-butylthio-, and t-butylthio-.

"Heterocycloalkyl" means a non-aromatic heterocyclic ring containing 3-8 or 5-6 ring atoms, being saturated or having one or more degrees of unsaturation and containing one or more heteroatom substitutions selected from O, S, and/or N. Such a ring may be optionally fused to one or more other heterocycloalkyl ring(s) or cycloalkyl ring(s). Examples of "heterocycloalkyl" moieties include, but are not limited to, aziridinyl, thiiranyl, oxiranyl, azetidinyl, oxetanyl, thietanyl, tetrahydrofuranyl, dihydropyranyl, tetrahydropyranyl, 1,4-dioxanyl, 1,3-dioxanyl, piperidinyl, piperazinyl, 2,4-piperazinedionyl, pyrrolidinyl, pyrrolinyl, imidazolidinyl, pyrazolidinyl, pyrazolinyl, morpholinyl, thiomorpholinyl, tetrahydrothiopyranyl, tetrahydrothienyl, and the like.

"Aryl" refers to optionally substituted monocyclic or fused bicyclic groups having 6 to 14 carbon atoms and having at least one aromatic ring that complies with Hückel's Rule. Examples of "aryl" groups are phenyl, naphthyl, indenyl, dihydroindenyl, anthracenyl, phenanthrenyl, and the like. "Heteroaryl" means an optionally substituted aromatic monocyclic ring or fused bicyclic ring system wherein at least one ring complies with Hückel's Rule, has the specified number of ring atoms, and that ring contains at least one heteroatom selected from N, O, and/or S. Examples of 5-membered "heteroaryl" groups include furanyl, thienyl, pyrrolyl, imidazolyl, pyrazolyl, triazolyl, tetrazolyl, thiazolyl, oxazolyl, isoxazolyl, oxadiazolyl, thiadiazolyl, and isothiazolyl. Examples of 6-membered "heteroaryl" groups include oxopyridyl, pyridinyl, pyridazinyl, pyrazinyl, and pyrimidinyl. Examples of 6,6-fused "heteroaryl" groups include quinolinyl, isoquinolinyl, quinoxalinyl, cinnolinyl, phthalazinyl, quinazolinyl, 1,5-naphthyridinyl, 1,6-naphthyridinyl, 1,7-naphthyridinyl, 1,8-naphthyridinyl, and pteridinyl. Examples of 6,5-fused "heteroaryl" groups include benzofuranyl, benzothienyl, benzimidazolyl, benzthiazolyl, indolizinyl, indolyl, isoindolyl, and indazolyl.

For the avoidance of doubt, all bicyclic ring systems may be attached at any suitable position on either ring.

As used herein, "halogen" or "halo" refers to F, Cl, Br, or I.

"Optionally substituted" indicates that a group, such as alkyl, alkenyl, alkynyl, cycloalkyl, cycloalkenyl, bicycloalkyl, alkoxy, heterocycloalkyl, aryl, or heteroaryl, may be unsubstituted, or the group may be substituted with one or more substituent(s) as defined. In the case where groups may be selected from a number of alternative groups the selected groups may be the same or different.

The term "independently" means that where more than one substituent is selected from a number of possible substituents, those substituents may be the same or different.

That is, each substituent is separately selected from the entire group of recited possible substituents (e.g. a group of substituents provided herein for various aryl or heteroaryl is halogen, —$CF_3$, $(C_1-C_4)$alkyl, hydroxyl, and $(C_1-C_4)$alkoxy).

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

Suitably, $R^1$ and $R^2$ are each independently selected from the group consisting of hydrogen, $(C_1-C_8)$alkyl, $(C_2-C_8)$alkenyl, $(C_2-C_8)$alkynyl, $(C_3-C_8)$cycloalkyl, $(C_5-C_8)$cycloalkenyl, $(C_6-C_{10})$bicycloalkyl, heterocycloalkyl, $(C_3-C_8)$cycloalkyl$(C_1-C_6)$alkyl, $(C_5-C_8)$cycloalkenyl$(C_1-C_6)$alkyl, heterocycloalkyl$(C_1-C_6)$alkyl, aryl, heteroaryl, aryl$(C_1-C_6)$alkyl, and heteroaryl$(C_1-C_6)$alkyl;

wherein any $(C_1-C_8)$alkyl, $(C_2-C_8)$alkenyl, or $(C_2-C_8)$alkynyl is optionally substituted one to three times, independently, by —$CF_3$, cyano, —$CO_2(C_1-C_4)$alkyl, —$CONH(C_1-C_4)$alkyl, —$CON(C_1-C_4)$alkyl$(C_1-C_4)$alkyl, —$SO_2(C_1-C_4)$alkyl, —$SO_2NH(C_1-C_4)$alkyl, —$SO_2N(C_1-C_4)$alkyl$(C_1-C_4)$alkyl, amino, $(C_1-C_4)$alkylamino, $((C_1-C_4)$alkyl$)((C_1-C_4)$alkyl)amino, hydroxyl, or $(C_1-C_4)$alkoxy;

and wherein any cycloalkyl, cycloalkenyl, bicycloalkyl, or heterocycloalkyl group is optionally substituted one to three times, independently, by $(C_1-C_4)$alkyl, $(C_1-C_4)$haloalkyl, cyano, —$CO_2(C_1-C_4)$alkyl, —$CONH(C_1-C_4)$alkyl, —$CON(C_1-C_4)$alkyl$(C_1-C_4)$alkyl, —$SO_2(C_1-C_4)$alkyl, —$SO_2NH(C_1-C_4)$alkyl, —$SO_2N(C_1-C_4)$alkyl$(C_1-C_4)$alkyl, amino, $(C_1-C_4)$alkylamino, $((C_1-C_4)$alkyl$)((C_1-C_4)$alkyl)amino, hydroxyl, $(C_1-C_4)$alkoxy, aryl, or aryl$(C_1-C_4)$alkyl; wherein the aryl moiety of said aryl or aryl$(C_1-C_4)$alkyl is optionally substituted one to three times, independently, by halogen, —$CF_3$, $(C_1-C_4)$alkyl, hydroxyl, or $(C_1-C_4)$alkoxy;

and wherein any aryl or heteroaryl group is optionally substituted one to three times, independently, by halogen, $(C_1-C_6)$alkyl, $(C_3-C_6)$cycloalkyl, $(C_5-C_6)$cycloalkenyl, $(C_1-C_6)$haloalkyl, cyano, —$CO_2(C_1-C_4)$alkyl, —$CONH(C_1-C_4)$alkyl, —$CON(C_1-C_4)$alkyl$(C_1-C_4)$alkyl, —$SO_2(C_1-C_4)$alkyl, —$SO_2NH(C_1-C_4)$alkyl, —$SO_2N(C_1-C_4)$alkyl$(C_1-C_4)$alkyl, amino, $(C_1-C_4)$alkylamino, $((C_1-C_4)$alkyl$)((C_1-C_4)$alkyl)amino, hydroxyl, $(C_1-C_4)$alkoxy, $(C_1-C_4)$alkylthio-, aryl, heteroaryl, aryl$(C_1-C_4)$alkyl, or heteroaryl$(C_1-C_4)$alkyl;

wherein any aryl or heteroaryl moiety of said aryl, heteroaryl, aryl$(C_1-C_4)$alkyl, or heteroaryl$(C_1-C_4)$alkyl is optionally substituted one to three times, independently, by halogen, —$CF_3$, $(C_1-C_4)$alkyl, hydroxyl, or $(C_1-C_4)$alkoxy;

and wherein any $(C_3-C_6)$cycloalkyl is optionally substituted one to three times, independently, by $(C_1-C_4)$alkyl, aryl, or heteroaryl;
   wherein said aryl or heteroaryl is optionally substituted one to three times, independently, by halogen, —$CF_3$, $(C_1-C_4)$alkyl, hydroxyl, or $(C_1-C_4)$alkoxy.

In another embodiment, $R^1$ and $R^2$ are each independently selected from the group consisting of hydrogen, $(C_1-C_6)$alkyl, $(C_3-C_7)$cycloalkyl, $(C_7-C_9)$bicycloalkyl, heterocycloalkyl, $(C_3-C_7)$cycloalkyl$(C_1-C_4)$alkyl, phenyl, heteroaryl, phenyl$(C_1-C_4)$alkyl, and heteroaryl$(C_1-C_4)$alkyl;
   wherein any $(C_1-C_6)$alkyl group is optionally substituted one to three times, independently, by $(C_3-C_6)$cycloalkyl, —$CF_3$, cyano, —$CO_2(C_1-C_4)$alkyl, hydroxyl, or $(C_1-C_4)$alkoxy;
   and wherein any cycloalkyl, bicycloalkyl, or heterocycloalkyl group is optionally substituted one to three times, independently, by $(C_1-C_4)$alkyl, —$CF_3$, cyano, —$CO_2(C_1-C_4)$alkyl, hydroxyl, $(C_1-C_4)$alkoxy, phenyl, or phenyl$(C_1-C_2)$alkyl; wherein the phenyl moiety of said phenyl or phenyl$(C_1-C_2)$alkyl is optionally substituted one to three times, independently, by halogen, —$CF_3$, $(C_1-C_4)$alkyl, hydroxyl, or $(C_1-C_4)$alkoxy;
   and wherein any phenyl or heteroaryl group is optionally substituted one to three times, independently, by halogen, $(C_1-C_6)$alkyl, $(C_3-C_6)$cycloalkyl, —$CF_3$, cyano, —$CO_2(C_1-C_4)$alkyl, —$SO_2(C_1-C_4)$alkyl, hydroxyl, $(C_1-C_4)$alkoxy, $(C_1-C_4)$alkylthio-, phenyl, heteroaryl, phenyl$(C_1-C_4)$alkyl, or heteroaryl$(C_1-C_4)$alkyl;
      wherein any phenyl or heteroaryl moiety of said phenyl, heteroaryl, phenyl$(C_1-C_4)$alkyl, or heteroaryl$(C_1-C_4)$alkyl is optionally substituted one to three times, independently, by halogen, —$CF_3$, or $(C_1-C_4)$alkyl;
      and wherein any $(C_3-C_6)$cycloalkyl is optionally substituted one to three times, independently, by $(C_1-C_4)$alkyl, phenyl, or heteroaryl;
         wherein said phenyl or heteroaryl is optionally substituted one to three times, independently, by halogen, —$CF_3$, or $(C_1-C_4)$alkyl.

In a further embodiment, $R^1$ is selected from the group consisting of $(C_1-C_6)$alkyl, $(C_3-C_7)$cycloalkyl, $(C_7-C_9)$bicycloalkyl, heterocycloalkyl, $(C_3-C_7)$cycloalkyl$(C_1-C_2)$alkyl, phenyl, heteroaryl, and phenyl$(C_1-C_2)$alkyl; wherein any cycloalkyl or heterocycloalkyl group is optionally substituted one to two times, independently, by $(C_1-C_4)$alkyl, —$CF_3$, hydroxyl, or $(C_1-C_4)$alkoxy, and wherein any phenyl or heteroaryl group is optionally substituted one to two times, independently, by halogen, $(C_1-C_4)$alkyl, —$CF_3$, cyano, —$CO_2(C_1-C_4)$alkyl, hydroxyl, $(C_1-C_4)$alkoxy, or $(C_1-C_4)$alkylthio-. In yet a further embodiment, $R^1$ is phenyl optionally substituted one to two times, independently, by halogen, $(C_1-C_4)$alkyl, —$CF_3$, cyano, —$CO_2(C_1-C_4)$alkyl, hydroxyl, $(C_1-C_4)$alkoxy, or $(C_1-C_4)$alkylthio-. In yet a further embodiment, $R^1$ is furanyl, thienyl, pyrrolyl, imidazolyl, pyrazolyl, triazolyl, tetrazolyl, thiazolyl, oxazolyl, isoxazolyl, oxadiazolyl, thiadiazolyl, or isothiazolyl optionally substituted by halogen, $(C_1-C_4)$alkyl, —$CF_3$, $(C_3-C_6)$cycloalkyl, phenyl, halophenyl, phenyl$(C_1-C_4)$alkyl, halophenyl$(C_1-C_4)$alkyl, cyano, —$CO_2(C_1-C_4)$alkyl, $(C_1-C_4)$alkoxy, or $(C_1-C_4)$alkylthio-; wherein said $(C_3-C_6)$cycloalkyl is optionally substituted by $(C_1-C_4)$alkyl. In yet a further embodiment, $R^1$ is thiadiazolyl optionally substituted by halogen, $(C_1-C_4)$alkyl, —$CF_3$, $(C_3-C_6)$cycloalkyl, phenyl, halophenyl, phenyl$(C_1-C_4)$alkyl, cyano, —$CO_2(C_1-C_4)$alkyl, $(C_1-C_4)$alkoxy, or $(C_1-C_4)$alkylthio-; wherein said $(C_3-C_6)$cycloalkyl is optionally substituted by $(C_1-C_4)$alkyl. In yet a further embodiment, $R^1$ is thiadiazolyl optionally substituted by halogen, $(C_1-C_4)$alkyl, —$CF_3$, $(C_3-C_6)$cycloalkyl, phenyl, cyano, —$CO_2(C_1-C_4)$alkyl, or $(C_1-C_4)$alkoxy; wherein said $(C_3-C_6)$cycloalkyl is optionally substituted by $(C_1-C_4)$alkyl. In selected embodiments, $R^1$ is 5-cyclohexyl-1,3,4-thiadiazol-2-yl or 5-phenyl-1,3,4-thiadiazol-2-yl.

In another embodiment, $R^2$ is hydrogen or $(C_1-C_4)$alkyl. In selected embodiments, $R^2$ is hydrogen or methyl. In another selected embodiment, $R^2$ is hydrogen.

In another embodiment, $R^1$ and $R^2$ taken together with the nitrogen to which they are attached represent a 5- to 7-membered saturated or unsaturated ring optionally containing one other heteroatom which is oxygen, nitrogen, or sulfur; wherein said ring is optionally fused to a $(C_3-C_8)$cycloalkyl, heterocycloalkyl, aryl, or heteroaryl ring. In a further embodiment, $R^1$ and $R^2$ taken together with the nitrogen to which they are attached represent a 5- to 6-membered saturated or unsaturated ring optionally fused to a phenyl moiety. In a selected embodiment, $R^1$ and $R^2$ taken together with the nitrogen to which they are attached represent 1H-indol-1-yl or 2,3-dihydro-1H-indol-1-yl. In another selected embodiment, $R^1$ and $R^2$ taken together with the nitrogen to which they are attached represent 2,3-dihydro-1H-indol-1-yl.

In another embodiment, $R^1$ and $R^2$ taken together with the nitrogen to which they are attached represent a 6- to 10-membered bridged bicyclic ring system optionally fused to a $(C_3-C_8)$cycloalkyl, heterocycloalkyl, aryl, or heteroaryl ring. In a further embodiment, $R^1$ and $R^2$ taken together with the nitrogen to which they are attached represent a 7- to 9-membered bridged bicyclic ring system optionally fused to a phenyl moiety.

Suitably, $R^3$ is hydrogen, $(C_1-C_8)$alkyl, $(C_1-C_8)$haloalkyl, $(C_2-C_8)$alkenyl, $(C_2-C_8)$alkynyl, $(C_3-C_6)$cycloalkyl, $(C_5-C_6)$cycloalkenyl, $(C_3-C_6)$cycloalkyl$(C_1-C_4)$alkyl, $(C_5-C_6)$cycloalkenyl$(C_1-C_4)$alkyl, or aryl$(C_1-C_4)$alkyl; wherein the aryl moiety of the aryl$(C_1-C_4)$alkyl is optionally substituted one to three times, independently, by halogen, $(C_1-C_4)$alkyl, or —$CF_3$.

In another embodiment, $R^3$ is hydrogen, $(C_1-C_6)$alkyl, $(C_1-C_6)$haloalkyl, $(C_3-C_6)$cycloalkyl, $(C_3-C_6)$cycloalkyl$(C_1-C_4)$alkyl, or phenyl$(C_1-C_4)$alkyl; wherein the phenyl moiety of the phenyl$(C_1-C_4)$alkyl is optionally substituted one to three times, independently, by halogen, $(C_1-C_4)$alkyl, or —$CF_3$. In a further embodiment, $R^3$ is $(C_1-C_6)$alkyl or $(C_3-C_6)$cycloalkyl$(C_1-C_2)$alkyl. In selected embodiments, $R^3$ is ethyl, isobutyl, or sec-butyl. In further selected embodiments, $R^3$ is cyclopropylmethyl, cyclobutylmethyl, cyclopentylmethyl, or cyclohexylmethyl. In another selected embodiment, $R^3$ is cyclopropylmethyl. In a further embodiment, $R^3$ is phenyl$(C_1-C_4)$alkyl; wherein the phenyl moiety is optionally substituted one to two times, independently, by halogen, $(C_1-C_4)$alkyl, or —$CF_3$. In a selected embodiment, $R^3$ is phenethyl.

One particular embodiment of the invention is a compound of Formula (I) or a pharmaceutically acceptable salt thereof wherein:
   $R^1$ and $R^2$ are each independently selected from the group consisting of hydrogen, $(C_1-C_6)$alkyl, $(C_3-C_7)$cycloalkyl, $(C_7-C_9)$bicycloalkyl, heterocycloalkyl, $(C_3-C_7)$cycloalkyl$(C_1-C_4)$alkyl, phenyl, heteroaryl, phenyl$(C_1-C_4)$alkyl, and heteroaryl$(C_1-C_4)$alkyl;
      wherein any $(C_1-C_6)$alkyl group is optionally substituted one to three times, independently, by $(C_3-C_6)$cycloalkyl, —$CF_3$, cyano, —$CO_2(C_1-C_4)$alkyl, hydroxyl, or $(C_1-C_4)$alkoxy;
      and wherein any cycloalkyl, bicycloalkyl, or heterocycloalkyl group is optionally substituted one to three times, independently, by $(C_1-C_4)$alkyl, —$CF_3$, cyano, —$CO_2(C_1-C_4)$alkyl, hydroxyl, $(C_1-C_4)$alkoxy, phenyl, or phenyl$(C_1-C_2)$alkyl;

wherein the phenyl moiety of said phenyl or phenyl$(C_1-C_2)$alkyl is optionally substituted one to three times, independently, by halogen, —$CF_3$, $(C_1-C_4)$alkyl, hydroxyl, or $(C_1-C_4)$alkoxy;

and wherein any phenyl or heteroaryl group is optionally substituted one to three times, independently, by halogen, $(C_1-C_6)$alkyl, $(C_3-C_6)$cycloalkyl, —$CF_3$, cyano, —$CO_2(C_1-C_4)$alkyl, —$SO_2(C_1-C_4)$alkyl, hydroxyl, $(C_1-C_4)$alkoxy, phenyl, heteroaryl, phenyl$(C_1-C_2)$alkyl, or heteroaryl$(C_1-C_2)$alkyl;

wherein any phenyl or heteroaryl moiety of said phenyl, heteroaryl, phenyl$(C_1-C_2)$alkyl, or heteroaryl$(C_1-C_2)$alkyl is optionally substituted one to three times, independently, by halogen, —$CF_3$, or $(C_1-C_4)$alkyl;

and wherein any $(C_3-C_6)$cycloalkyl is optionally substituted one to three times, independently, by $(C_1-C_4)$alkyl, phenyl, or heteroaryl;

wherein said phenyl or heteroaryl is optionally substituted one to three times, independently, by halogen, —$CF_3$, or $(C_1-C_4)$alkyl;

or $R^1$ and $R^2$ taken together with the nitrogen to which they are attached represent a 5- to 6-membered saturated or unsaturated ring optionally fused to a phenyl moiety;

or $R^1$ and $R^2$ taken together with the nitrogen to which they are attached represent a 7- to 9-membered bridged bicyclic ring system optionally fused to a phenyl moiety; and $R^3$ is $(C_1-C_6)$alkyl or $(C_3-C_6)$cycloalkyl$(C_1-C_2)$alkyl.

Another particular embodiment of the invention is a compound of Formula (I) or a pharmaceutically acceptable salt thereof wherein:

$R^1$ and $R^2$ taken together with the nitrogen to which they are attached represent a 5- to 6-membered saturated or unsaturated ring optionally fused to a phenyl moiety; and $R^3$ is $(C_1-C_6)$alkyl or $(C_3-C_6)$cycloalkyl$(C_1-C_2)$alkyl.

Another particular embodiment of the invention is a compound of Formula (I) or a pharmaceutically acceptable salt thereof wherein:

$R^1$ and $R^2$ taken together with the nitrogen to which they are attached represent 2,3-dihydro-1H-indol-1-yl; and $R^3$ is $(C_1-C_6)$alkyl or $(C_3-C_6)$cycloalkyl$(C_1-C_2)$alkyl.

Another particular embodiment of the invention is a compound of Formula (I) or a pharmaceutically acceptable salt thereof wherein:

$R^1$ is heteroaryl optionally substituted one to two times, independently, by halogen, $(C_1-C_4)$alkyl, —$CF_3$, cyano, —$CO_2(C_1-C_4)$alkyl, hydroxyl, or $(C_1-C_4)$alkoxy; wherein said heteroaryl is selected from the group consisting of furanyl, thienyl, pyrrolyl, imidazolyl, pyrazolyl, triazolyl, tetrazolyl, thiazolyl, oxazolyl, isoxazolyl, oxadiazolyl, thiadiazolyl, and isothiazolyl; and $R^2$ is hydrogen or methyl;

$R^3$ is $(C_1-C_6)$alkyl or $(C_3-C_6)$cycloalkyl$(C_1-C_2)$alkyl.

Another particular embodiment of the invention is a compound of Formula (I) or a pharmaceutically acceptable salt thereof wherein:

$R^1$ is thiadiazolyl optionally substituted by halogen, $(C_1-C_4)$alkyl, —$CF_3$, $(C_3-C_6)$cycloalkyl, phenyl, cyano, —$CO_2(C_1-C_4)$alkyl, or $(C_1-C_4)$alkoxy; wherein said $(C_3-C_6)$cycloalkyl is optionally substituted by $(C_1-C_4)$alkyl;

$R^2$ is hydrogen or methyl; and $R^3$ is $(C_1-C_6)$alkyl or $(C_3-C_6)$cycloalkyl$(C_1-C_2)$alkyl.

Specific compounds of Formula (I) are:
4-amino-N-[(1S,2E)-4-(2,3-dihydro-1H-indol-1-yl)-1-ethyl-4-oxo-2-buten-1-yl]tetrahydro-2H-pyran-4-carboxamide; and
4-amino-N-[(1S,2E)-4-(2,3-dihydro-1H-indol-1-yl)-1-(2-methylpropyl)-4-oxo-2-buten-1-yl]tetrahydro-2H-pyran-4-carboxamide;
or pharmaceutically acceptable salts thereof.

The invention also includes various isomers of the compounds of Formula (I) and mixtures thereof "Isomer" refers to compounds that have the same composition and molecular weight but differ in physical and/or chemical properties. The structural difference may be in constitution (geometric isomers) or in the ability to rotate the plane of polarized light (stereoisomers). The compounds according to Formula (I) contain one or more asymmetric centers, also referred to as chiral centers, and may, therefore, exist as individual enantiomers, diastereomers, or other stereoisomeric forms, or as mixtures thereof. All such isomeric forms are included within the present invention, including mixtures thereof.

Chiral centers may also be present in a substituent such as an alkyl group. Where the stereochemistry of a chiral center present in Formula (I), or in any chemical structure illustrated herein, is not specified the structure is intended to encompass any stereoisomer and all mixtures thereof. Thus, compounds according to Formula (I) containing one or more chiral centers may be used as racemic mixtures, enantiomerically enriched mixtures, or as enantiomerically pure individual stereoisomers.

Individual stereoisomers of a compound according to Formula (I) which contain one or more asymmetric centers may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). For example, α-deuterated α-amino acids are commercially available or may be prepared by conventional techniques (see for example: Elemes, Y. and Ragnarsson, U. *J. Chem. Soc., Perkin Trans.* 1, 1996, 6, 537-40). Employing such compounds according to Scheme 1 below will allow for the preparation of compounds of Formula (I) in which the hydrogen atom at the chiral center is replaced with a deuterium atom. Similarly, α-amino acids in which deuterium atoms have been incorporated into the sidechains are commercially available or may be prepared by conventional techniques. Employing such compounds according to Scheme 1 below will allow for the preparation of compounds of Formula (I) in which deuterium atoms have been incorporated in $R^3$. Additionally, replacement of the reagent lithium aluminum hydride with lithium aluminum deuteride according to Scheme 1 below will allow for deuterium substitution at the β-position of the butenamide of the compounds of Formula (I).

The term "solvate" refers to a complex of variable stoichiometry formed by a solute and a solvent. Such solvents for the purpose of the invention may not interfere with the biological activity of the solute. Examples of suitable solvents include, but are not limited to, water, methanol, ethanol and acetic acid. Preferably, the solvent used is a pharmaceutically acceptable solvent. Examples of suitable pharmaceutically acceptable solvents include, without limitation, water, ethanol and acetic acid. Solvates wherein water is the solvent molecule are typically referred to as "hydrates". Hydrates include compositions containing stoichiometric amounts of water, as well as compositions containing variable amounts of water. Solvates, particularly hydrates, of the compounds of Formula (I) and salts thereof, are within the scope of the invention.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formula (I) are preferably pharmaceutically acceptable. Suitable pharmaceutically acceptable salts can include acid or base addition salts. This invention also provides for the conversion of one pharmaceutically acceptable salt of a compound of this invention, e.g., a hydrochloride salt, into another pharmaceutically acceptable salt of a compound of this invention, e.g., a sulfate salt.

As used herein, the term "pharmaceutically acceptable" means a compound which is suitable for pharmaceutical use. Salts and solvates (e.g. hydrates and hydrates of salts) of the compounds of the invention which are suitable for use in medicine are those wherein the counterion or associated solvent is pharmaceutically acceptable. However, salts and solvates having non-pharmaceutically acceptable counterions or associated solvents are within the scope of the present invention, for example, for use as intermediates in the preparation of other compounds of the invention and their salts and solvates.

Compounds of Formula (I) have one or more nitrogen(s) basic enough to form pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include acetate, aspartate, benzenesulfonate, benzoate, bicarbonate, bitartrate, bromide, calcium edetate, camsylate, carbonate, chloride, citrate, dihydrochloride, edetate, edisylate, estolate, esylate, formate, fumarate, galacturonate, gluceptate, gluconate, glutamate, glycollylarsanilate, hexanoate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, propionate, salicylate, stearate, subacetate, succinate, sulfate, tannate, tartrate, teoclate, and tosylate salts.

Other iterations of compounds of the invention have an acidic functional group, one acidic enough to form salts. Representative salts include pharmaceutically acceptable metal salts such as sodium, potassium, lithium, calcium, magnesium, aluminum, and zinc salts; carbonates and bicarbonates of a pharmaceutically acceptable metal cation such as sodium, potassium, lithium, calcium, magnesium, aluminum, and zinc; pharmaceutically acceptable organic primary, secondary, and tertiary amines including aliphatic amines, aromatic amines, aliphatic diamines, and hydroxy alkylamines such as methylamine, ethylamine, 2-hydroxyethylamine, diethylamine, triethylamine, ethylenediamine, ethanolamine, diethanolamine, cyclohexylamine, triethanolamine, choline, arginine, lysine, and histidine.

Other non-pharmaceutically acceptable salts, e.g. trifluoroacetate, may be used, for example in the isolation of compounds of the invention, and are included within the scope of this invention.

The invention includes within its scope all possible stoichiometric and non-stoichiometric forms of the salts of the compounds of Formula (I).

It will be appreciated by those skilled in the art that certain protected derivatives of compounds of Formula (I), which may be made prior to a final deprotection stage, may not possess pharmacological activity as such, but may, in certain instances, be administered orally or parenterally and thereafter metabolized in the body to form compounds of the invention which are pharmacologically active. Such derivatives may therefore be described as "prodrugs". Further, certain compounds of the invention may act as prodrugs of other compounds of the invention. All protected derivatives and prodrugs of compounds of the invention are included within the scope of the invention. Examples of suitable pro-drugs for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention. Preferred "pro-moieties" for compounds of the invention include: ester, carbonate ester, hemi-ester, phosphate ester, nitro ester, sulfate ester, sulfoxide, amide, carbamate, azo-, phosphamide, glycoside, ether, acetal, and ketal derivatives of the compounds of Formula (I).

The compounds of the invention inhibit the cathepsin C enzyme and can be useful in the treatment of conditions wherein the underlying pathology is (at least in part) attributable to cathepsin C involvement or in conditions wherein cathepsin C inhibition offers some clinical benefit even though the underlying pathology is not (even in part) attributable to cathepsin C involvement. Examples of such conditions include COPD, rheumatoid arthritis, osteoarthritis, asthma, and multiple sclerosis. Accordingly, in another aspect the invention is directed to methods of treating such conditions.

The methods of treatment of the invention comprise administering an effective amount of a compound of the invention to a patient in need thereof.

As used herein, "treatment" in reference to a condition means: (1) the amelioration of the condition being treated or one or more of the biological manifestations of the condition being treated, (2) the interference with (a) one or more points in the biological cascade that leads to or is responsible for the condition being treated or (b) one or more of the biological manifestations of the condition being treated, or (3) the alleviation of one or more of the symptoms or effects associated with the condition being treated.

An "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, "patient" refers to a human or animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the amount administered and the duration such regimens are administered, for a compound of the invention depend on the condition being treated, the severity of the condition being treated, the age and physical condition of the patient being treated, the medical history of the patient to be treated, the nature of concurrent therapy, the particular route of administration chosen, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Typical daily dosages range from 1 mg to 1000 mg.

The invention includes the use of compounds of the invention for the preparation of a composition for treating or ameliorating diseases mediated by the cathepsin C enzyme in a subject in need thereof, wherein the composition comprises a mixture of one or more of the compounds of the invention and an optional pharmaceutically acceptable excipient.

The invention further includes the use of compounds of the invention as an active therapeutic substance, in particular in the treatment of diseases mediated by the cathepsin C enzyme. Specifically, the invention includes the use of compounds of the invention in the treatment of COPD, rheumatoid arthritis, osteoarthritis, asthma, and multiple sclerosis.

In another aspect, the invention includes the use of compounds of the invention in the manufacture of a medicament for use in the treatment of the above disorders.

Compositions

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form wherein each physically discrete unit contains an effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds. Conversely, the pharmaceutical compositions of the invention typically contain more than one pharmaceutically acceptable excipient. However, in certain embodiments, the pharmaceutical compositions of the invention contain one pharmaceutically acceptable excipient.

As used herein, "pharmaceutically acceptable excipient" means a material, composition or vehicle involved in giving form or consistency to the composition and which is safe when administered to a patient. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compounds of the invention and the pharmaceutically acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder may be administered to the patient via a reservoir dry powder inhaler (RDPI) having a reservoir suitable for storing multiple (un-metered doses) of medicament in dry powder form. RDPIs typically include a means for metering each medicament dose from the reservoir to a delivery position. For example, the metering means may comprise a metering cup, which is movable from a first position where the cup may be filled with medicament from the reservoir to a second position where the metered medicament dose is made available to the patient for inhalation.

Alternatively, the dry powder may be presented in capsules (e.g. gelatin or plastic), cartridges, or blister packs for use in a multi-dose dry powder inhaler (MDPI). MDPIs are inhalers wherein the medicament is comprised within a multi-dose pack containing (or otherwise carrying) multiple defined doses (or parts thereof) of medicament. When the dry powder is presented as a blister pack, it comprises multiple blisters for containment of the medicament in dry powder form. The blisters are typically arranged in regular fashion for ease of release of the medicament therefrom. For example, the blisters may be arranged in a generally circular fashion on a disc-form blister pack, or the blisters may be elongate in form, for example comprising a strip or a tape. Each capsule, cartridge, or blister may, for example, contain between 20 μg-10 mg of the compound of the invention.

Aerosols may be formed by suspending or dissolving a compound of the invention in a liquified propellant. Suitable propellants include halocarbons, hydrocarbons, and other liquified gases. Representative propellants include: trichlorofluoromethane (propellant 11), dichlorofluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropylalcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Methods of Preparation.

The compounds of Formula (I) may be obtained by using synthetic procedures illustrated in the Schemes below or by drawing on the knowledge of a skilled organic chemist. The synthesis provided in these Schemes are applicable for producing compounds of the invention having a variety of different $R^1$-$R^3$ groups employing appropriate precursors, which are suitably protected if need be, to achieve compatibility with the reactions outlined herein. Subsequent deprotection, where needs be, and then affords compounds of the nature generally disclosed. While the Schemes are shown with compounds only of Formula (I), they are illustrative of processes that may be used to make the compounds of the invention.

Compounds names were generated using the software naming program ACD/Name Pro V6.02 available from Advanced Chemistry Development, Inc., 110 Yonge Street, 14$^{th}$ Floor, Toronto, Ontario, Canada, MSC 1T4 (http://www.acdlabs.com/).

As shown in Scheme 1, the compounds of Formula (I) can be prepared in a multi-step sequence starting from a Boc-protected α-amino acid, such as the commercially available (2S)-2-({[(1,1-dimethylethyl)oxy]carbonyl}amino)butanoic acid or N-(tert-butoxycarbonyl)-L-leucine. Formation of an appropriate amide derivative, such as a Weinreb amide, using an appropriate amine or amine salt, such as N,O-dimethylhydroxylamine hydrochloride, with an appropriate coupling reagent, such as 1,1'-carbonyldiimidazole, and an appropriate base, such as DIPEA, in an appropriate solvent, such as $CH_2Cl_2$, followed by reduction with an appropriate reducing agent, such as $LiAlH_4$, in an appropriate solvent, such as $Et_2O$, provides the requisite aldehyde. Enoate formation with an appropriate olefinating reagent, such as methyl(triphenylphosphoranylidene)acetate, in an appropriate solvent, such as $Et_2O$, is followed by ester hydrolysis with an appropriate reagent, such as LiOH, in an appropriate solvent system, such as THF, MeOH, and water. This is followed by amide bond formation with an appropriate acyclic or cyclic amine and an appropriate coupling reagent or reagents, such as ®T3P or the BOP reagent, and an appropriate base, such as $Et_3N$ or DIPEA, in an appropriate solvent, such as $CH_2Cl_2$ or DMF. Boc deprotection with an appropriate reagent, such as TFA, is followed by coupling of the liberated amine with 4-((tert-butoxycarbonyl)amino)tetrahydro-2H-pyran-4-carboxylic acid, with an appropriate coupling reagent or reagents, such as ®T3P, and an appropriate base, such as $Et_3N$, in an appropriate solvent, such as $CH_2Cl_2$. Boc deprotection with an appropriate reagent, such as HCl, results in the formation of the desired compounds of Formula (I), which may be isolated as the corresponding salt form or converted to the free base using conventional techniques.

Scheme 1

Reagents and conditions: a) HCl•HN(OCH$_3$)CH$_3$, DIPEA, 1,1'-carbonyldiimidazole, CH$_2$Cl$_2$; b) LiAlH$_4$, Et$_2$O; c)Ph$_3$P═CHCO$_2$CH$_3$, Et$_2$O; d) LiOH, THF, MeOH, water; e) HNR$^1$R$^2$, ®T3P, EtOAc, Et$_3$N, CH$_2$Cl$_2$ or HNR$^1$R$^2$, BOP reagent, DIPEA, DMF; f) TFA, CH$_2$Cl$_2$; g) 4-((tert-butoxycarbonyl)amino)tetrahydro-2H-pyran-4-carboxylic acid, ®T3P, EtOAc, Et$_3$N, CH$_2$Cl$_2$; h) HCl, isopropanol.

SYNTHETIC EXAMPLES

The invention will now be described by reference to the following examples which are merely illustrative and are not to be construed as a limitation of the scope of the present invention. All temperatures are given in degrees Celsius, all solvents are highest available purity and all reactions run under anhydrous conditions in an argon (Ar) or nitrogen (N$_2$) atmosphere where necessary.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. The Combi-Flash® system used for purification in this application was purchased from Isco, Inc. CombiFlash® purification was carried out using prepacked silica gel columns, a detector with UV wavelength at 254 nm and a variety of solvents or solvent combinations. Preparative HPLC was performed using a Gilson Preparative System with variable wavelength UV detection or an Agilent Mass Directed AutoPrep (MDAP) system with both mass and variable wavelength UV detection. A variety of reverse phase columns, e.g., Luna 5u C18(2) 100 A, SunFire C18, XBridge C18 were used in the purification with the choice of column support dependent upon the conditions used in the purification. The compounds are eluted using a gradient of CH$_3$CN and water. Neutral conditions used an CH$_3$CN and water gradient with no additional modifier, acidic conditions used an acid modifier, usually 0.1% TFA (added to both the CH$_3$CN and water) and basic conditions used a basic modifier, usually 0.1% NH$_4$OH (added to the water). Analytical HPLC was run using an Agilent system with variable wavelength UV detection using reverse phase chromatography with an CH$_3$CN and water gradient with a 0.05 or 0.1% TFA modifier (added to each solvent). LC-MS was determined using either a PE Sciex Single Quadrupole LC/MS API-150a, or Waters ZQ instruments. The compound is analyzed using a reverse phase column, e.g., Thermo Aquasil/Aquasil C18, Acquity UPLC C18, Thermo Hypersil Gold eluted using an CH$_3$CN and water gradient with a low percentage of an acid modifier such as 0.02% TFA or 0.1% formic acid.

Nuclear magnetic resonance spectra were recorded at 400 MHz using a Bruker AVANCE 400 or Brucker DPX400 spectrometer. CDCl$_3$ is deuteriochloroform, DMSO-d$_6$ is hexadeuteriodimethylsulfoxide, and MeOD is tetradeuteriomethanol. Chemical shifts are reported in parts per million ($\delta$) downfield from the internal standard tetramethylsilane (TMS) or calibrated to the residual proton signal in the NMR solvent (e.g., CHCl$_3$ in CDCl$_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz. Melting points were determined using an Electrothermal 9100 apparatus (Electrothermal Engineering Ltd.).

Heating of reaction mixtures with microwave irradiations was carried out on a Smith Creator (purchased from Personal Chemistry, Foxboro, Mass., now owned by Biotage), an Emrys Optimizer (purchased from Personal Chemistry) or an Explorer (purchased from CEM, Matthews, N.C.) microwave.

Cartridges or columns containing polymer based functional groups (acid, base, metal chelators, etc) can be used as part of compound workup. The "amine" columns or cartridges are used to neutralize or basify acidic reaction mixtures or products. These include NH2 Aminopropyl SPE-ed SPE Cartridges available from Applied Separations and diethylamino SPE cartridges available from United Chemical Technologies, Inc.

Abbreviations are listed in the table below. All other abbreviations are as described in the ACS Style Guide (American Chemical Society, Washington, D.C., 1986).

Table of Abbreviations

| | |
|---|---|
| BOP reagent: benzotriazole-1-yl-oxy-tris-(dimethylamino)-phosphonium hexafluorophosphate | ®T3P: propane phosphonic acid anhydride |
| Et$_3$N: triethylamine | CH$_2$Cl$_2$: dichloromethane |
| DIPEA: N,N-diisopropylethylamine | DMSO: dimethyl sulfoxide |
| TFA: trifluoroacetic acid | THF: tetrahydrofuran |
| HCl: hydrochloric acid | DMF: N,N-dimethylformamide |
| NaHCO$_3$: sodium bicarbonate | EtOAc: ethyl acetate |
| Na$_2$SO$_4$: sodium sulfate | Et$_2$O: diethyl ether |
| LiAlH$_4$: lithium aluminum hydride | MeOH: methanol |
| mL: milliliter(s) | CH$_3$CN: acetonitrile |
| min: minute(s) | aq.: aqueous |
| h: hour(s) | M: molar |
| g: gram(s) | mmol: millimole(s) |
| mg: milligram(s) | RT: room temperature |

INTERMEDIATE COMPOUNDS

Intermediate 1

1,1-dimethylethyl ((1S)-1-{[methylmethyloxy)amino]carbonyl}propyl)carbamate To a solution of (2S)-2-({[(1,1-dimethylethyl)oxy]carbonyl}amino)butanoic acid (2.50 g, 12.3 mmol) in THF (15.0 mL) was added 1,1'-carbonyldiimidazole (2.39 g, 14.8 mmol) portionwise over about 10 min. After stirring 30 min at RT, a solution of N,O-dimethylhydroxylamine hydrochloride (1.32 g, 13.5 mmol) and DIPEA (2.36 mL, 13.5 mmol) in DMF (4.0 mL) was added. The reaction mixture was stirred for 2 h at RT, followed by concentration in vacuo. The residue was diluted with EtOAc (50 mL) and washed with 1 M aq. HCl (2×20 mL), saturated aq. NaHCO$_3$ (2×20 mL), and brine (20 mL). The organic layer was dried over Na$_2$SO$_4$, filtered, and concentrated in vacuo to afford the title compound (2.60 g, 88%) as a clear, colorless oil. LC-MS m/z 247 (M+H)$^+$, 0.94 min (ret time).

Intermediate 2

1,1-dimethylethyl[(1S)-1-formylpropyl]carbamate

To a solution of LiAlH₄ (0.453 g, 11.9 mmol) in Et₂O (20 mL) at 0° C. was added dropwise a solution of 1,1-dimethylethyl ((1S)-1-{[methyl(methyloxy)amino]carbonyl}-propyl)carbamate (2.67 g, 10.8 mmol) in Et₂O (15 mL). The reaction mixture was stirred for 30 min at 0° C. and quenched with EtOAc (6.5 mL) followed by 5% aq. potassium bisulfate (6.5 mL). The reaction mixture was washed with 1 M aq. HCl (3×10 mL), saturated aq. NaHCO₃ (3×10 mL), and brine (10 mL). The organic layer was dried over Na₂SO₄, filtered, and concentrated in vacuo to afford the title compound as a clear, colorless oil.

Intermediate 3 methyl (2E,4S)-4-({[(1,1-dimethylethyl)oxy]carbonyl}amino)-2-hexenoate

To a stirred solution of methyl(triphenylphosphoranylidene)acetate (4.35 g, 13.0 mmol) in Et₂O (25 mL) at RT was added a solution of Intermediate 2 in Et₂O (15 mL). The reaction mixture was stirred at RT overnight. The solid was removed by filtration and the solution was concentrated in vacuo. Purification via flash column chromatography (0-50% EtOAc/hexanes) afforded the title compound (1.44 g, 55% over two steps) as a clear, colorless oil. LC-MS m/z 244 (M+H)⁺, 0.98 min (ret time).

Intermediate 4

(2E,4S)-4-({[(1,1-dimethylethyl)oxy]carbonyl}amino)-2-hexenoic acid

LiOH (2.95 g, 123 mmol) was added to a solution of methyl (2E,4S)-4-({[(1,1-dimethylethyl)oxy]carbonyl}amino)-2-hexenoate (6 g, 24.66 mmol) in THF (50 mL), MeOH (10.00 mL), and water (50.0 mL). The reaction was stirred overnight at RT. After 18.5 h, the reaction mixture was concentrated under reduced pressure to remove the THF and MeOH. Water (40 mL) was added, and aqueous mixture was adjusted to pH=3 with 6 M aq. HCl, as measured by pH paper. EtOAc (80 mL) was added, the layers were separated, and the aqueous layer was extracted with EtOAc (2×40 mL). The combined organic layers were dried over Na₂SO₄, concentrated under reduced pressure, and dried under high vacuum, giving 6.09 g of the title compound. LC-MS m/z 230 (M+H)⁺, 0.77 min (ret time).

Intermediate 5

1,1-dimethylethyl[(1S,2E)-4-(2,3-dihydro-1H-indol-1-yl)-1-ethyl-4-oxo-2-buten-1-yl]carbamate A solution of 50 wt %®T3P in EtOAc (22.00 mL, 37.0 mmol) was added dropwise via addition funnel to a solution of (2E,4S)-4-({[(1,1-dimethylethyl)oxy]carbonyl}-amino)-2-hexenoic acid (5.65 g, 24.64 mmol), 2,3-dihydro-1H-indole (2.76 mL, 24.64 mmol), and Et₃N (11 mL, 79 mmol) in CH₂Cl₂ (90 mL) at 0° C. (bath temp). The ice bath was removed, and the reaction was stirred at RT. After 30 min, the reaction was quenched by dropwise addition of saturated aq. NaHCO₃ (50 mL). The layers were separated, and the reaction was washed with 10% citric acid (1×50 mL). The organic layer was concentrated under a stream of nitrogen, and the residue was purified by flash column chromatography, giving 7.21 g (89%) of the title compound. LC-MS m/z 331 (M+H)⁺, 1.05 (ret time).

Intermediate 6

[(1S,2E)-4-(2,3-dihydro-1H-indol-1-yl)-1-ethyl-4-oxo-2-buten-1-yl]amine trifluoroacetate TFA (25 mL, 324 mmol) was added to a solution of 1,1-dimethylethyl[(1S,2E)-4-(2,3-dihydro-1H-indol-1-yl)-1-ethyl-4-oxo-2-buten-1-yl]carbamate (7.21 g, 21.82 mmol) in CH₂Cl₂ (25 mL). The reaction was stirred at RT. After 3.5 h, CH₂Cl₂ (200 mL) was added, and the reaction was concentrated under reduced pressure and dried under high vacuum. LC-MS m/z 231 (M+H)⁺, 0.69 (ret time).

Intermediate 7

1,1-dimethylethyl[4-({[(1S,2E)-4-(2,3-dihydro-1H-indol-1-yl)-1-ethyl-4-oxo-2-buten-1-yl]amino}carbonyl)tetrahydro-2H-pyran-4-yl]carbamate A solution of 50 wt % T3P in EtOAc (1.3 mL, 2.184 mmol) was added dropwise to a solution of [(1S,2E)-4-(2,3-dihydro-1H-indol-1-yl)-1-ethyl-4-oxo-2-buten-1-yl]amine trifluoroacetate (500 mg, 1.452 mmol), 4-((tert-butoxycarbonyl)amino)tetrahydro-2H-pyran-4-carboxylic acid (356 mg, 1.452 mmol), and Et₃N (1 mL, 7.21 mmol) in CH₂Cl₂ (5 mL) at 0° C. (bath temp). The ice bath was removed, and the reaction was stirred at RT. After 1 h 20 min, the reaction mixture was washed with saturated aq. NaHCO₃ (1×5 mL) and 10% citric acid (1×5 mL). The organic layer was concentrated under a stream of nitrogen, and the residue was purified by flash column chromatography, giving 251 mg (38%) of the title compound. LC-MS m/z 458 (M+H)⁺, 0.96 (ret time).

Intermediate 8

N²-{[(1,1-dimethylethyl)oxy]carbonyl}-N¹-methyl-N¹-methyloxy)-L-leucinamide To a solution of N-(tert-butoxycarbonyl)-L-leucine (3.00 g, 13.0 mmol) in THF (25.0 mL) was added 1,1'-carbonyldiimidazole (2.52 g, 15.6 mmol) portionwise over about 10 min. After stirring 1 h at RT, a solution of N,O-dimethylhydroxylamine hydrochloride (1.39 g, 14.3 mmol) and DIPEA (2.49 mL, 14.3 mmol) in DMF (6.0 mL) was added. The reaction mixture was stirred for 2.5 h at RT, followed by concentration in vacuo. The residue was diluted with EtOAc (50 mL) and washed with 1 M aq. HCl (2×20 mL), saturated aq. NaHCO₃ (2×20 mL), and brine (20 mL). The organic layer was dried over Na₂SO₄, filtered, and concentrated in vacuo to afford the title compound (2.34 g, 66%) as a clear, colorless oil. LC-MS m/z 275 (M+H)⁺, 1.17 min (ret time).

Intermediate 9

1,1-dimethylethyl[(1S)-1-formyl-3-methylbutyl]carbamate

To a solution of LiAlH₄ (0.356 g, 9.38 mmol) in Et₂O (20 mL) at 0° C. was added dropwise a solution of N²-{[(1,1-dimethylethyl)oxy]carbonyl}-N¹-methyl-N¹-(methyloxy)-L-leucinamide (2.34 g, 8.53 mmol) in Et₂O (15 mL). The reaction mixture was stirred for 30 min at 0° C. and quenched with EtOAc (6 mL) followed by 5% aq. potassium bisulfate (6 mL). The reaction mixture was washed with 1 M aq. HCl (2×10 mL), saturated aq. NaHCO₃ (2×10 mL), and brine (10 mL). The organic layer was dried over Na₂SO₄, filtered, and concentrated in vacuo to afford the title compound as a clear, colorless oil.

Intermediate 10 methyl (2E,4S)-4-({[(1,1-dimethylethyl)oxy]carbonyl}amino)-6-methyl-2-heptenoate To a stirred solution of methyl(triphenylphosphoranylidene)acetate (3.42 g, 10.2 mmol) in Et₂O (25 mL) at RT was added a solution of Intermediate 9 in Et₂O (15 mL). The reaction mixture was stirred for 15 h at RT. The solid was removed by filtration and the solution was concentrated in vacuo. Purification via flash column chromatography (0-50% EtOAc/hexanes) afforded the title compound (1.74 g, 75% over two steps) as a clear, colorless oil. LC-MS m/z 272 (M+H)⁺, 1.22 min (ret time).

Intermediate 11

(2E,4S)-4-({[(1,1-dimethylethyl)oxy]carbonyl}amino)-6-methyl-2-heptenoic acid To a solution of methyl (2E,4S)-4-({[(1,1-dimethylethyl)oxy]carbonyl}amino)-6-methyl-2-heptenoate (5.00 g, 18.43 mmol) in THF (15 mL), MeOH (15.0 mL), and water (15 mL) was added LiOH (2.206 g, 92.00 mmol). After stirring for 2 h at RT, the reaction mixture was concentrated in vacuo. The reaction mixture was acidified with 6 M aq. HCl to pH=5 and then extracted with EtOAc. The organic layer was washed with water, dried over Na₂SO₄, filtered, and concentrated in vacuo to afford the title compound (4.7 g, 99%) as a white semi-solid. LC-MS m/z 158 (M+H-Boc)⁺, 0.94 min (ret time).

Intermediate 12

1,1-dimethylethyl[(1S,2E)-4-(2,3-dihydro-1H-indol-1-yl)-1-(2-methylpropyl)-4-oxo-2-buten-1-yl]carbamate

To a solution of (2E,4S)-4-({[(1,1-dimethylethyl)oxy]carbonyl}amino)-6-methyl-2-heptenoic acid (4.70 g, 18.26 mmol) in DMF (30.0 mL) were added BOP reagent (8.08 g, 18.26 mmol) and DIPEA (6.38 mL, 36.5 mmol). After stirring at RT for 5 min, 2,3-dihydro-1H-indole (2.053 mL, 18.26 mmol) was added and stirring continued overnight. The reaction mixture was diluted with water and extracted with EtOAc. The organic layer was washed with brine, dried over Na₂SO₄, filtered, concentrated in vacuo and purified by flash column chromatography (0-20% EtOAc/hexanes) to afford the title compound (4.83 g, 74%) as a white solid. LC-MS m/z 359 (M+H)⁺, 1.18 min (ret time).

Intermediate 13

[(1S,2E)-4-(2,3-dihydro-1H-indol-1-yl)-1-(2-methylpropyl)-4-oxo-2-buten-1-yl]amine trifluoroacetate

-continued

To a solution of 1,1-dimethylethyl[(1S,2E)-4-(2,3-dihydro-1H-indol-1-yl)-1-(2-methylpropyl)-4-oxo-2-buten-1-yl]carbamate (3.21 g, 8.95 mmol) in CH$_2$Cl$_2$ (10.0 mL) was added TFA (10 mL, 130 mmol). The reaction mixture was stirred for 17.5 h at RT and then concentrated under reduced pressure and dried under high vacuum to afford the title compound. LC-MS m/z 259 (M+H)$^+$, 0.76 min (ret time).

Intermediate 14

1,1-dimethylethyl[4-({[(1S,2E)-4-(2,3-dihydro-1H-indol-1-yl)-1-(2-methylpropyl)-4-oxo-2-buten-1-yl]amino}carbonyl)tetrahydro-2H-pyran-4-yl]carbamate

A solution of 50 wt %®T3P in EtOAc (1.2 mL, 2.016 mmol) was added dropwise to a solution of [(1S,2E)-4-(2,3-dihydro-1H-indol-1-yl)-1-(2-methylpropyl)-4-oxo-2-buten-1-yl]amine trifluoroacetate (500 mg, 1.343 mmol), 4-((tert-butoxycarbonyl)amino)tetrahydro-2H-pyran-4-carboxylic acid (329 mg, 1.343 mmol), and Et$_3$N (0.93 mL, 6.71 mmol) in CH$_2$Cl$_2$ (5 mL) at 0° C. (bath temp). The ice bath was removed, and the reaction was stirred at RT. After 1 h 20 min, the reaction was washed with saturated aq. NaHCO$_3$ (1×5 mL) and 10% citric acid (1×5 mL). The organic layer was concentrated under a stream of nitrogen, and the residue was purified by flash column chromatography, giving 204 mg (31%) of the title compound. LC-MS m/z 486 (M+H)$^+$, 1.07 min (ret time).

Compounds of Formula (I)

Example 1

4-amino-N-[(1S,2E)-4-(2,3-dihydro-1H-indol-1-yl)-1-ethyl-4-oxo-2-buten-1-yl]tetrahydro-2H-pyran-4-carboxamide hydrochloride

A solution of concentrated aq. HCl (0.23 mL, 2.76 mmol) was added to a solution of 1,1-dimethylethyl[4-({[(1S,2E)-4-(2,3-dihydro-1H-indol-1-yl)-1-ethyl-4-oxo-2-buten-1-yl]amino}carbonyl)tetrahydro-2H-pyran-4-yl]carbamate (251 mg, 0.549 mmol) in isopropanol (2.5 mL). The reaction flask was fitted with an air condenser, and the reaction mixture was heated to 65° C. (bath temp) for 1 h 45 min. The solvent was evaporated under reduced pressure. Water (5 mL) was added to the residue, and the mixture was concentrated under reduced pressure at 65° C. Water (2 mL) was added to the residue, and the mixture was lyophilized, giving 193.3 mg (89%) of the title compound. LC-MS m/z 358 (M+H)$^+$, 0.68 (ret time). $^1$H NMR (400 MHz, METHANOL-d$_4$) δ ppm 8.14 (br. s., 1H); 7.25 (d, J=7.03 Hz, 1H); 7.18 (t, J=7.53 Hz, 1H); 7.02-7.09 (m, 1H); 6.83 (dd, J=15.18, 6.65 Hz, 1H); 6.49 (d, J=14.8 Hz, 1H); 4.56 (d, J=7.28 Hz, 1H); 4.22 (br. s., 2H); 3.95 (d, J=7.53 Hz, 1H); 3.88-3.94 (m, 1H); 3.71-3.78 (m, 2H); 3.23 (br. s., 2H); 2.39-2.46 (m, 2H); 1.79-1.86 (m, 2H); 1.75 (s, 1H); 1.72 (d, J=8.28 Hz, 1H); 1.00 (t, J=7.40 Hz, 3H).

Example 2

4-amino-N-[(1S,2E)-4-(2,3-dihydro-1H-indol-1-yl)-1-(2-methylpropyl)-4-oxo-2-buten-1-yl]tetrahydro-2H-pyran-4-carboxamide hydrochloride -continued A solution of concentrated aq. HCl (0.22 mL, 2.64 mmol) was added to a solution of 1,1-dimethylethyl[4-({[(1S,2E)-4-(2,3-dihydro-1H-indol-1-yl)-1-(2-methylpropyl)-4-oxo-2-buten-1-yl]amino}carbonyl)tetrahydro-2H-pyran-4-yl]carbamate (251 mg, 0.517 mmol) in isopropanol (2.5 mL). The reaction flask was fitted with an air condenser, and the reaction mixture was heated to 65° C. (bath temp). After 1 h 45 min, the solvent was evaporated under reduced pressure at 60° C. Water (5 mL) was added to the residue, and the mixture was concentrated under reduced pressure at 65° C. Water (2 mL) was added to the residue, and the mixture was lyophilized, giving 130.6 mg (60%) of the title compound. LC-MS m/z 386 (M+H)$^+$, 0.79 (ret time). $^1$H NMR (400 MHz, METHANOL-d$_4$) δ ppm 8.15 (d, J=7.03 Hz, 1H); 7.25 (d, J=7.03 Hz, 1H); 7.18 (t, J=7.65 Hz, 1H); 7.06 (t, J=7.91 Hz, 1H); 6.81 (dd, J=15.18, 6.40 Hz, 1H); 6.49 (br. s., 1H); 4.73-4.85 (m, 2H); 4.21 (t, J=8.28 Hz, 2H); 3.91-3.97 (m, 2H); 3.70-3.77 (m, 2H); 3.25-3.21 (m, 2H); 2.35-2.48 (m, 2H); 1.82 (d, J=14.31 Hz, 2H); 1.63-1.71 (m, 2H); 1.50-1.57 (m, 1H); 0.98 (dd, J=11.92, 6.40 Hz, 6H).

Biological Background:
Biological Assay(s)

The compounds according to Formula (I) are cathepsin C inhibitors, which indirectly inhibit the activity of serine proteases that are activated by cathepsin C, such as NE. The compounds according to Formula (I), therefore, are useful in the treatment of COPD and other conditions involving cathepsin C and/or such serine proteases. The biological activity of the compounds according to Formula (I) can be determined using any suitable assay for determining the activity of a candidate compound as a cathepsin C inhibitor or for determining the ability of a candidate compound to prevent the cathepsin C mediated activation of certain serine proteases, as well as suitable tissue and in vivo models.

A. Transpeptidation of Leucine-Leucine-O-Methyl (LLOM) Cell-Based Luminescence Viability Assay
Principle:

Cathepsin C has been shown to catalyze the transpeptidation of dipeptidyl methyl-O-esters within the lysosomes of cells from the monocytic lineage such as HL60, U937 or THP1 causing a membranolytic effect that results in cell death (D L. Thiele, P. Lipsky PNAS 1990 Vol. 87, pp. 83-87). This mechanism was used to assess Cathepsin C in cells activity in the presence of the compounds of the invention.

Frozen HL-60 cells were resuspended at $1.25 \times 10^5$ cells/mL in fresh prewarmed Iscove's modified Dulbeccos' medium (IMDM, contains 25 mM glutamine) with 20% FBS. This suspension was dispensed (8 μL) into white low volume 384 well plates. Plates were previously stamped with 100 mL of compound at a top concentration of 2.5 mM and serially diluted 1:3. Control and blank wells contained 100 mL of DMSO. Each well then received 2 μL of a fresh 1.25 mM solution of leucine-leucine-OMethyl (LLOM, Bachem) in IMDM plus 25 mM HEPES (final concentration LLOM 250 μM). The plates were covered and incubated for 4 h at 37° C. in a 5% CO$_2$ incubator, then removed and equilibrated to room temperature for 10 min. Cell viability was determined with a CellTiter-Glo luminescent assay (Promega) according to the manufacturer's instructions. Cell viability was compared to controls containing no LLOM (100%).

B. Recombinant Cathepsin C In Vitro Assay:

The activity of recombinant human cathepsin C was measured by the cleavage of a fluorogenic substrate, H-Ser-Tyr-AMC. Briefly, 24 μM cathepsin C was incubated with test compound (e.g. inhibitor) in a buffer consisting of 50 mM sodium acetate, 30 mM sodium chloride, 1 mM CHAPS, 1 mM dithiothreitol, 1 mM EDTA, pH 5.5 at room temperature for one hour. After one hour of incubating test compound with cathepsin C, the activity assay was initiated by the addition of an equal volume of 0.010 mM H-Ser-Tyr-AMC in the same buffer. After one hour, the activity assay was stopped by the addition of 1/5 volume of 100 μM E-64. The reaction product was measured on a fluorescence reader set at an excitation wavelength of 360 nm and emission wavelength of 460 nm and equipped with a 400 nm dichroic mirror.

The compounds of Examples 1 and 2 each exhibited 50% cathepsin C inhibition at a concentration of less than 1 nM in an average of two experiments.

C. Mouse Cigarette Smoke Exposure In Vivo Assay:
Mouse Cigarette Smoke Exposure and Drug Administration:

Beginning at 3-4 months of age, female C57BL/6 mice (Jackson Laboratory, Bar Harbor, Me.) received nose-only exposure to 4% cigarette smoke from 3R4F cigarettes (College of Agriculture, Reference Cigarette Program, University of Kentucky), for 2 h/day, 5 days/week for 18 weeks. Smoke was generated by a Baumgartner-Jaeger CSM 2070i Smoking Machine (CH Technologies Inc., Westwood, N.J.). During exposure to smoke or air (sham controls), mice were maintained in restraining tubes containing stainless steel nose cone inserts. Two hours following the final smoke exposure, bronchoalveolar lavage (BAL) fluid (n=3 per treatment group) was collected. During the final 6 weeks of the 18 week exposure, mice were administered drug or vehicle alone (1% methylcellulose/25 mM citrate, pH 4.0) orally, twice daily (at 11 and 13 hour intervals), 7 days/week. Sham-exposed mice received vehicle alone, while smoke-exposed mice received one of the following treatments: vehicle alone, the Compound of Example 1 at 1, 10 or 30 mg/kg, or the Compound of Example 2 at 1, 10 or 30 mg/kg. Mice received the first daily dose of drug or vehicle alone up to 1 hour prior to the initiation of smoke/sham exposure.

Bronchoalveolar Lavage:

Animals were euthanized using i.p. injection of 0.1 ml Fatal Plus (Vortech Pharmaceuticals, Dearborn, Mich.) and the trachea cannulated with a 3-in. section of PE90 tubing (BD, Franklin Lakes, N.J.), to which was attached a blunted 21-gauge needle connected to a 3-way stopcock (Baxter Healthcare, Deerfield, Ill.). Four 1 mL aliquots of ice cold PBS were injected and removed sequentially through the tubing separately, and the BAL fluid centrifuged at 140×g for 2 min. Cell pellets isolated from the four aliquots were combined and total cells counted using a hemocytometer. Differential cell analysis was performed on cytospins using Wright-Geimsa stain.

Figure 1:
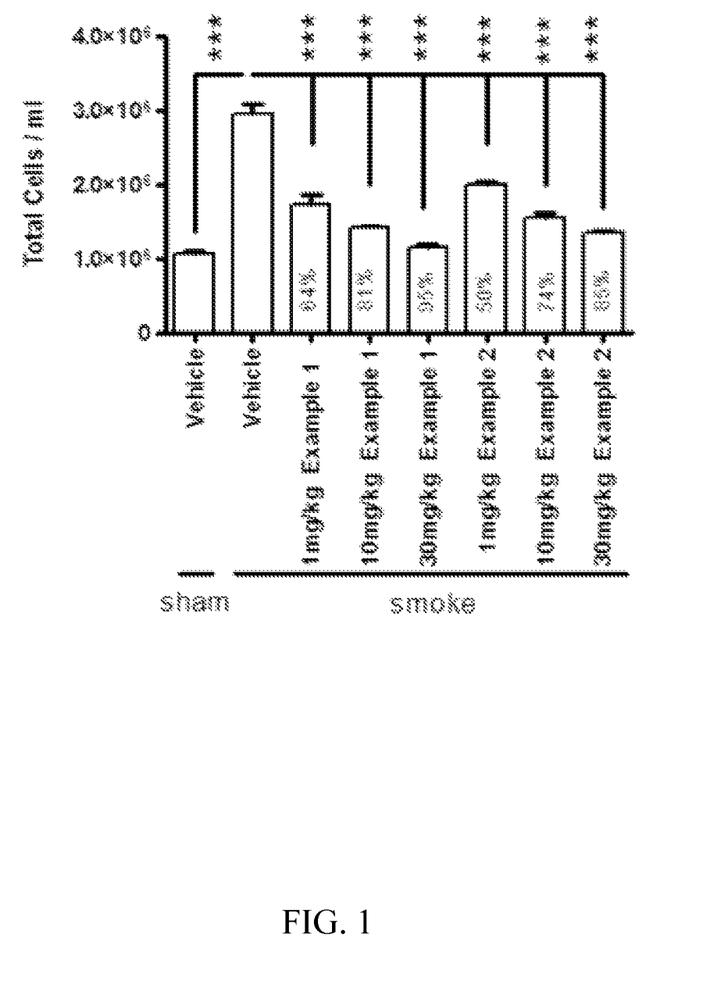
FIG. 1 shows the accumulation of total leukocytes in the Bronchoalveolar Lavage Fluid of C57BL/6 Mice following twice daily oral administration of the compounds of Example 1 and 2 at the indicated doses for the final 6 weeks during 18 weeks of cigarette smoke exposure.
Figure 2:
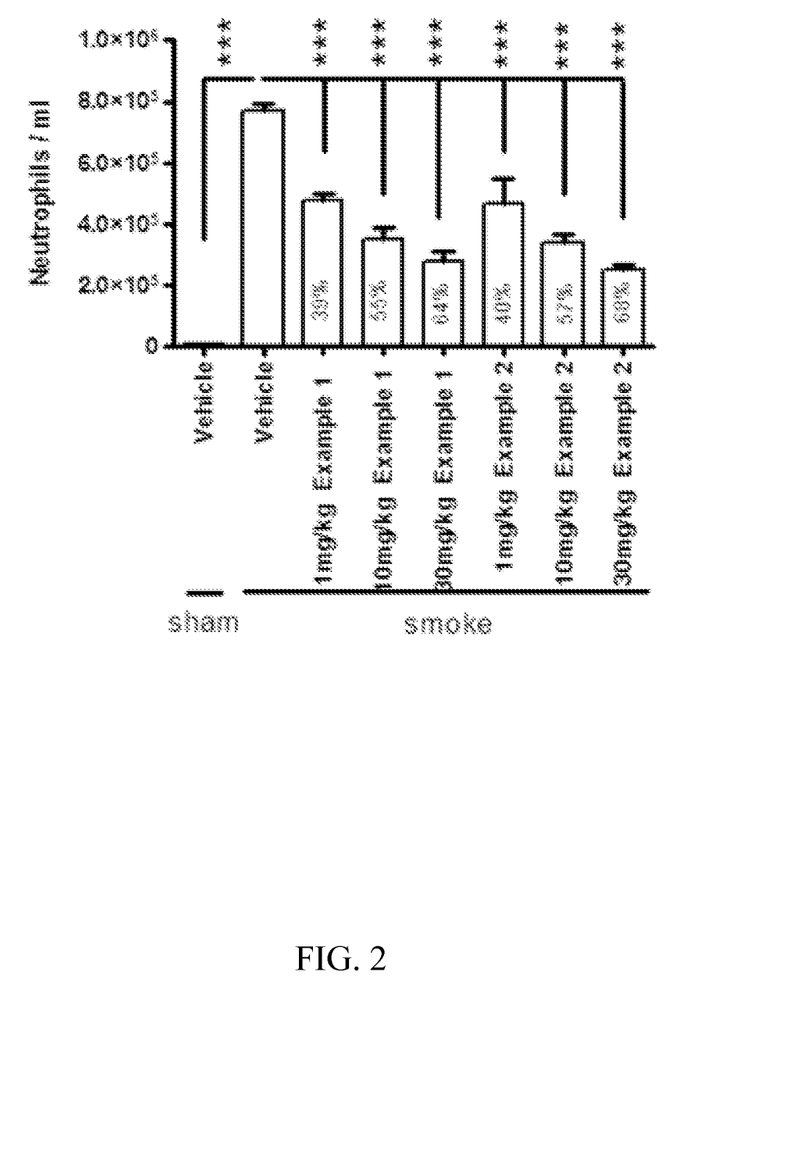
FIG. 2 shows the accumulation of neutrophils in the Bronchoalveolar Lavage Fluid of C57BL/6 Mice following twice daily oral administration of the compounds of Example 1 and 2 at the indicated doses for the final 6 weeks during 18 weeks of cigarette smoke exposure.
Figure 3:
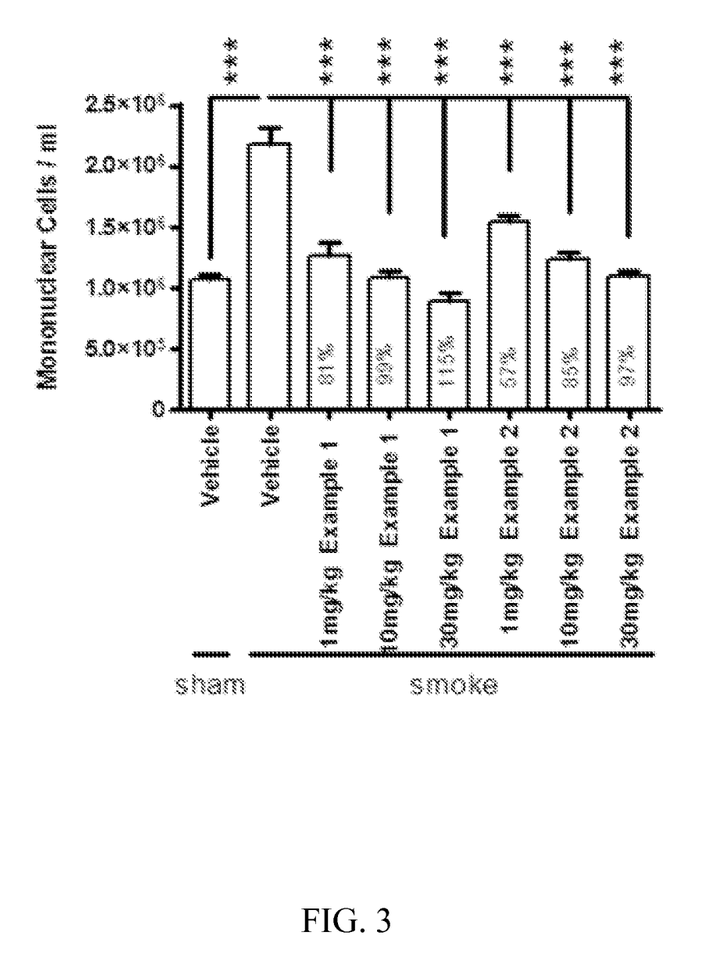
FIG. 3 shows the accumulation of mononuclear cells in the Bronchoalveolar Lavage Fluid of C57BL/6 Mice following twice daily oral administration of the compounds of Example 1 and 2 at the indicated doses for the final 6 weeks during 18 weeks of cigarette smoke exposure.

Statistical Analysis:

Data are presented in FIGS. 1, 2, and 3 as the mean±S.E.M. Statistical significance was determined using a one-way ANOVA with a Bonferroni post-test. Values of p<0.05 were considered significant. *, p<0.05; , p<0.01; *, p<0.001. Percent values shown indicate percent inhibition of the window between vehicle-treated/smoke-exposed animals and vehicle-treated/sham-exposed animals.

The compounds of the invention are believed to be useful in therapy as defined above and to not have unacceptable or untoward effects when used in compliance with a permitted therapeutic regime.

The foregoing examples and assay have been set forth to illustrate the invention, not limit it. What is reserved to the inventors is to be determined by reference to the claims.

What is claimed is:

1. A compound which is 4-amino-N-[(1S,2E)-4-(2,3-dihydro-1H-indol-1-yl)-1-ethyl-4-oxo-2-buten-1-yl]tetrahydro-2H-pyran-4-carboxamide, represented by the formula:

or a pharmaceutically acceptable salt thereof.

2. A compound which is 4-amino-N-[(1S,2E)-4-(2,3-dihydro-1H-indol-1-yl)-1-ethyl-4-oxo-2-buten-1-yl]tetrahydro-2H-pyran-4-carboxamide, represented by the formula:

3. A pharmaceutical composition which comprises the compound or salt according to claim 1, and a pharmaceutically acceptable excipient.

4. A pharmaceutical composition which comprises the compound according to claim 2, and a pharmaceutically acceptable excipient.

5. A process for preparing the composition as defined in claim 3, the process comprising mixing the compound or salt with the pharmaceutically acceptable excipient.

6. A process for preparing the composition as defined in claim 4, the process comprising mixing the compound with the pharmaceutically acceptable excipient.

* * * * *